US009522190B2

(12) United States Patent
Lee et al.

(10) Patent No.: US 9,522,190 B2
(45) Date of Patent: Dec. 20, 2016

(54) POLYMERIC NANOPARTICLE SOLUTION COMPOSITION AND ITS MANUFACTURING PROCESS

(71) Applicant: SAMYANG BIOPHARMACEUTICALS CORPORATION, Seoul (KR)

(72) Inventors: Sa-Won Lee, Daejeon (KR); Joong-Woong Cho, Daejeon (KR); Gyeong-Hae Kim, Suwon-si (KR); Min-Hyo Seo, Daejeon (KR)

(73) Assignee: SAMYANG BIOPHARMACEUTICALS CORPORATION, Seoul (KR)

( * ) Notice: Subject to any disclaimer, the term of this patent is extended or adjusted under 35 U.S.C. 154(b) by 15 days.

(21) Appl. No.: 14/362,234

(22) PCT Filed: Dec. 7, 2012

(86) PCT No.: PCT/KR2012/010637

§ 371 (c)(1),
(2) Date: Jun. 2, 2014

(87) PCT Pub. No.: WO2013/089394

PCT Pub. Date: Jun. 20, 2013

(65) Prior Publication Data

US 2014/0335194 A1 Nov. 13, 2014

(30) Foreign Application Priority Data

Dec. 16, 2011 (KR) ........................ 10-2011-0136809

(51) Int. Cl.

| | |
|---|---|
| ***A61K 47/34*** | (2006.01) |
| ***A61K 9/51*** | (2006.01) |
| ***A61K 31/337*** | (2006.01) |
| ***A61K 31/436*** | (2006.01) |
| ***A61K 9/14*** | (2006.01) |

(52) U.S. Cl.

CPC ................. *A61K 47/34* (2013.01); *A61K 9/14* (2013.01); *A61K 9/5146* (2013.01); *A61K 31/337* (2013.01); *A61K 31/436* (2013.01); *A61K 9/5153* (2013.01)

(58) Field of Classification Search

CPC ...... A61K 9/5146; A61K 31/337; A61K 9/14; A61K 31/436; A61K 47/34; A61K 9/5153

See application file for complete search history.

(56) References Cited

U.S. PATENT DOCUMENTS

| | | | | |
|---|---|---|---|---|
| 5,674,837 | A * | 10/1997 | Kirkpatrick ............ | C07K 9/003 514/19.3 |
| 7,311,901 | B2 | 12/2007 | Seo | |
| 7,879,317 | B2 | 2/2011 | Seo | |
| 8,349,306 | B2 | 1/2013 | Seo | |
| 8,778,322 | B2 | 7/2014 | Seo | |
| 2010/0168186 | A1* | 7/2010 | Duncan ................ | A61K 9/0019 514/356 |
| 2010/0203114 | A1 | 8/2010 | Kwon | |
| 2011/0257253 | A1 | 10/2011 | Seo | |
| 2012/0276169 | A1 | 11/2012 | Kang | |

FOREIGN PATENT DOCUMENTS

| | | |
|---|---|---|
| CN | 1571816 | 1/2005 |
| CN | 1780865 | 5/2006 |
| EP | 1698327 A1 * | 9/2006 |
| KR | 10-2003-0045611 | 6/2003 |
| KR | 10-2004-0047146 | 6/2004 |
| KR | 10-2006-0013377 | 2/2006 |
| KR | 10-0704548 | 4/2007 |
| KR | 10-2010-0057007 | 5/2010 |
| KR | 10-2011-0079518 | 7/2011 |
| WO | 03/033592 | 4/2003 |
| WO | WO 2006103691 A1 * | 10/2006 |

OTHER PUBLICATIONS

Lee et al. ("Ionically Fixed Polymeric Nanoparticles as a Novel Drug Carrier," in Pharmaceutical Research, vol. 24, No. 8, Aug. 2007).*

Holvoet et al. "Preparation and evaluation of paclitaxel-containing liposomes" in Pharmazie, 62:126-132, 2007).*

Ionically fixed polymeric nanoparticles as a novel drug carrier, Pharmaceutical Research, vol. 24, No. 8, Aug. 2007, p. 1508-1516.

The Search Report dated May 29, 2015 attached to the Office Action Jun. 8, 2015, State Intellectual Property Office of the P.R.C, Chinese Patent Application No. 201280061834.2.

The extended European Search Report dated Jul. 28, 2015, European Patent Office, European Patent Application No. 12857983.6.

* cited by examiner

*Primary Examiner* — Blessing M Fubara

(74) *Attorney, Agent, or Firm* — Lex IP Meister, PLLC

(57) ABSTRACT

Disclosed are a polymeric drug carrier-containing pharmaceutical composition with enhanced stability in its solution state and a method for stabilizing the same. More particularly, disclosed are a pharmaceutical aqueous solution composition for storage under refrigeration containing a polymeric drug carrier comprising an amphiphilic block copolymer comprised of a hydrophilic block and a hydrophobic block, and a polylactic acid derivative fixed with a di- or tri-valent metal ion at its terminal carboxyl group and having preservation stability for at least 6 months, preferably at least 12 months when stored under refrigeration, and a method for stabilizing the same.

10 Claims, No Drawings

POLYMERIC NANOPARTICLE SOLUTION COMPOSITION AND ITS MANUFACTURING PROCESS

FIELD OF THE INVENTION

The present invention relates to a polymeric drug carrier-containing pharmaceutical composition in an aqueous solution state with enhanced stability and a method for stabilizing the same. More particularly, it relates to a pharmaceutical aqueous solution composition containing a polymeric drug carrier comprising an amphiphilic block copolymer which is comprised of a hydrophilic block and a hydrophobic block, and a polylactic acid derivative fixed with a di- or tri-valent metal ion at its terminal carboxyl group and having storage stability for at least 6 months, preferably at least 12 months when stored under refrigeration, and a method for stabilizing the same.

BACKGROUND OF THE INVENTION

In order to achieve the desired therapeutic effect of a bioactive agent, an appropriate amount of the administered drug should be delivered into the target cells in a body. For this, a submicronic particulate drug delivery system using biodegradable polymers is being studied and as its typical example, nanoparticle system and polymeric micelle system have been reported as a technology of reducing side effects and enhancing efficiencies by modifying in vivo distribution of an intravenously-injected drug. Such drug delivery system can adjust the release of a drug into the target organs, tissues, or cells, and has been reported to have excellent biocompatibility and enhance the solubility of an insoluble drug and the bioavailability of a drug.

However, the polymer usually used for the preparation of polymeric nanoparticles or polymeric micelles is currently a diblock amphiphilic block copolymer (mPEG-PLA) comprised of a hydrophilic block such as monomethoxypolyethyleneglycol (mPEG) and a hydrophobic block such as polylactic acid (PLA), and since this polymer tends to be hydrolyzed in an aqueous solution, its final product is provided in the form of a lyophilized powder or cake.

Thus, in using as a drug carrier the above polymer which is stored in a solid state after lyophilization, it is inconvenient because it has to be dissolved again in a distilled water right before the use thereof. Moreover, the lyophilization increases the manufacturing costs and it causes a stability issue because there are possibilities of concentration change and microbe contamination during the reconstitution thereof.

Accordingly, if a final product can be provided in an aqueous solution state by enhancing the stability of a polymeric drug carrier in the aqueous solution state, it is expected that its manufacturing time will be shortened and it will be readily applicable as a drug carrier.

SUMMARY OF THE INVENTION

Hence, the inventors have conducted researches for developing polymeric drug carrier aqueous solution agents which can not only reduce their preparation time but also be ready to use without any reconstitution or dilution, and while storing polymeric nanoparticle aqueous solution compositions at a room temperature and under refrigeration, they evaluated the physicochemical stability of the nanoparticles and as a result, surprisingly, they found that the compositions were stably maintained for at least 6 months, preferably at least 12 months when stored under refrigeration, and thus completed the invention.

It is an object of the invention to provide a method for stabilizing a pharmaceutical composition containing a polymeric drug carrier in the aqueous solution state, and a stabilized pharmaceutical composition in an aqueous solution form.

More particularly, it is an object of the invention to provide a method for stabilizing a pharmaceutical composition in an aqueous solution form comprising a polymeric drug carrier, a bioactive agent entrapped inside the drug carrier, and an aqueous solvent, comprising storing the pharmaceutical composition in an aqueous solution form under refrigeration.

It is another object of the invention to provide a pharmaceutical composition in an aqueous solution form stabilized by the above method.

Since the polymeric drug carrier-containing pharmaceutical composition according to the invention can be provided in a physicochemically stable aqueous solution state for at least 6 months, preferably at least 12 months when stored under refrigeration, it can be easily prepared with no need for undergoing lyophilization process and it can be conveniently used as an injection solution without the reconstitution thereof.

DETAILED DESCRIPTION OF THE INVENTION

As one aspect for achieving the above objects, the invention is directed to a method for stabilizing a pharmaceutical composition in an aqueous solution form comprising a polymeric drug carrier, a bioactive agent entrapped inside the drug carrier, and an aqueous solvent, comprising a step of storing the pharmaceutical composition under refrigeration, and wherein the polymeric drug carrier comprises (a) a non-ionic amphiphilic block copolymer which is comprised of a hydrophilic block and a hydrophobic block, and (b) a polylactic acid derivative having a di- or tri-valent metal ion substituted for a monovalent metal ion which is bound to a terminal carboxyl group of the polylactic acid derivative.

As another aspect, the invention is directed to a pharmaceutical composition in an aqueous solution form stabilized by the above method.

Preferably, the invention is directed to a pharmaceutical composition in an aqueous solution form for use as a final product.

Preferably, the invention is directed to a pharmaceutical composition in an aqueous solution form which is a ready to use formulation.

As another aspect, the invention is directed to a pharmaceutical aqueous solution composition for storage under refrigeration, having storage stability for at least 6 months, preferably at least 12 months when stored under refrigeration, comprising a polymeric drug carrier, a bioactive agent entrapped inside the drug carrier, and an aqueous solvent, and wherein the polymeric drug carrier comprises (a) a non-ionic amphiphilic block copolymer which is comprised of a hydrophilic block and a hydrophobic block, and (b) a polylactic acid derivative having a di- or tri-valent metal ion substituted for a monovalent metal ion which is bound to the terminal carboxyl group of the polylactic acid derivative.

The invention will be further described in detail.

The inventors have confirmed that by storing a polymeric drug carrier aqueous solution composition containing an amphiphilic block copolymer under refrigeration, its stability in an aqueous solution state could be enhanced even when stored for a long period of time of at least 6 months, preferably at least 12 months. Therefore, the invention can provide a pharmaceutical composition in an aqueous solution form by the above stabilization method as a final product, and also provide it in a ready-to-use form.

Throughout the invention, the term "final product" refers to a material which can be provided immediately or be ready for use immediately without undergoing any subsequent processes such as lyophilization. In the prior arts regarding pharmaceutical compositions where amphiphilic block copolymers were used as a polymeric drug carrier, the pharmaceutical compositions in an aqueous solution form were treated as an intermediate product for producing a final product in a lyophilized form, but in this invention, a pharmaceutical composition in an aqueous solution form is provided as a final product which does not require any subsequent process such as lyophilization.

The pharmaceutical composition as a final product according to the invention can be used right away without undergoing any reconstitution or dilution processes, or it can be suitably diluted for use, depending on the drugs.

Throughout the invention, the term "ready-to-use pharmaceutical composition" refers to a pharmaceutical composition which can be used to a body right away without undergoing any reconstitution or dilution steps.

The pharmaceutical composition of the invention comprises a polymeric drug carrier, a bioactive agent entrapped inside the drug carrier, and an aqueous solvent as essential components thereof. Preferably, the polymeric drug carrier comprises a non-ionic amphiphilic block copolymer which is comprised of a hydrophilic block and a hydrophobic block, and a polylactic acid derivative fixed with a di- or tri-valent metal ion at its terminal carboxyl group.

Also, the pharmaceutical composition of the invention may further comprise a pH adjusting agent, an isotonic agent, a preservative, an analgesic, or a stabilizing agent.

The components of the pharmaceutical composition of the invention will be further described in detail.

The amphiphilic block copolymer in the invention may be any block copolymers where a hydrophilic block (A) and a hydrophobic block (B) are connected in A-B, A-B-A, or B-A-B type and preferably, it may be an A-B type diblock copolymer. The amphiphilic block copolymer may form a polymeric micelle in a core-shell form where the hydrophobic block forms a core and the hydrophilic block forms a shell.

The hydrophilic block of the amphiphilic block copolymer may be selected from the group consisting of polyalkylene glycol (e.g., polyethylene glycol), polyvinyl pyrrolidone, polyvinyl alcohol, and polyacryl amide, but is not limited thereto. Preferably, it may be polyethylene glycol and more preferably, it may be monomethoxy polyethylene glycol (mPEG). The hydrophilic polymer may have a weight average molecular weight in the range of 500 to 50,000 Daltons, preferably in the range of 500 to 20,000 Daltons and most preferably, in the range of 1,000 to 5,000 Daltons.

The hydrophobic block of the amphiphilic block copolymer is a polymer which is not dissolved in water and is biodegradable, and it may be selected from the group consisting of polylactide, polyglycolide, polydioxan-2-one, polycaprolactone, polylactic-co-glycolide, polylactic-co-caprolactone, polylactic-co-dioxan-2-one, and derivatives thereof where their carboxylic terminal group is substituted with a fatty acid, but is not limited thereto. Preferably, it may be either polylactide (PLA) or a copolymer of lactic acid and glycolic acid (PLGA). The hydroxyl terminal of the hydrophobic block may be protected by a fatty acid and for example, any one of acetic acid group, propionic acid group, butyric acid group, stearic acid group or palmitic acid group can be used. The hydrophobic block may have a weight average molecular weight in the range of 500 to 50,000 Daltons, preferably in the range of 500 to 20,000 Daltons and most preferably in the range of 1,000 to 5,000 Daltons.

The weight ratio of the hydrophilic block and the hydrophobic block which constitute the amphiphilic block copolymer may be 2:8 to 8:2. Also, the hydrophilic block may be preferably in the range of 40 to 70 wt %. If the hydrophilic block is less than 40 wt %, the polymer has a low solubility in water and thus it may be difficult to form micelles, and if it is more than 70 wt %, it is too highly hydrophilic, thereby decreasing the stability of the polymeric micelles and thus it may be difficult to be used as a solubilized composition.

The polylactic acid derivative fixed with a di- or tri-valent metal ion at its terminal carboxyl group may be obtained by reacting a polylactic acid derivative bound with a monovalent metal ion at its terminal carboxyl group with a di- or tri-valent metal ionic salt to substitute the monovalent metal ion with the di- or tri-valent metal ion.

The polylactic acid derivative bound with the monovalent metal ion at its terminal carboxyl group may be one, or two or more selected from the group consisting of polylactic acid, polylactide, polyglycolide, polymandelic acid, polycaprolactone, polydioxane-2-one, polyamino acid, polyorthoester, polyanhydride, and a copolymer thereof having a monovalent metal ion bound to its terminal carboxyl group, and particularly, it may be polylactic acid, polylactide, polyglycolide, polycaprolactone or polydioxan-2-one.

Preferably, the polylactic derivative bound with the monovalent metal ion at its terminal carboxyl group may be one, or two or more selected from the group consisting of polylactic acid, polylactide, polycaprolactone, a copolymer of lactic acid and mandelic acid, a copolymer of lactic acid and glycolic acid, a copolymer of lactic acid and caprolactone, and a copolymer of lactic acid and 1,4-dioxane-2-one having a monovalent metal ion bound to its terminal carboxyl group. More preferably, it may be selected from the group consisting of D,L-polylactic acid, a copolymer of D,L-lactic acid and glycolic acid, a copolymer of D,L-lactic acid and caprolactone, and a copolymer of D,L-lactic acid and 1,4-dioxan-2-one having a monovalent metal ion bound to its terminal carboxyl group.

In one embodiment, the polylactic derivative bound with the monovalent metal ion at its terminal carboxyl group may be those having at least one carboxylic acid salt at its one end and at least one selected from the group consisting of hydroxy, acetoxy, benzoyloxy, decanoyloxy, palmitoyloxy and alkoxy at its the other end. The carboxylic acid salt functions as a hydrophilic group in an aqueous solution of pH 4 or higher so that it can form polymeric micelles in the aqueous solution.

In one embodiment, the alkali metal ion may be a monovalent alkali metal ion of sodium, potassium, or lithium. Also, the polylactic acid derivative exists in a solid state at a room temperature, and it can be in a very stable form even when exposed to moisture in air because of its neutral pH.

Further, the polylactic acid derivative bound with the monovalent metal ion at its terminal carboxyl group may be in the form of a sodium salt, potassium salt or lithium salt obtained by a condensation reaction in the absence of a catalyst followed by neutralization with sodium carbonate, sodium hydrogen carbonate, potassium carbonate, potassium hydrogen carbonate, or lithium carbonate.

The polylactic acid derivative in the invention functions to enhance the drug entrapment efficiency by hardening the inside of the core of a micelle in which the drug is entrapped. Also, the polylactic acid derivative may form a micelle by hydrophilic portions and hydrophobic portions present in the inside of the polylactic acid derivative molecule which are balanced when dissolved in an aqueous solution. For this, preferably, the polylactic acid derivative of the invention is not dissolved in an aqueous solution of pH 4 or less but it is dissolved in an aqueous solution of pH 4 or higher thereby to form a micelle, and it may have a number average molecular weight of 500 to 2,500 Daltons. If the molecular weight is less than 500 Daltons, it is completely dissolved in water so that the formation of a micelle itself may be difficult, and if the molecular weight exceeds 2,500 Daltons, it is too hydrophobic to be even dissolved in an aqueous solution so it may not form a micelle. The molecular weight of the polylactic acid derivative can be obtained by suitably adjusting a reaction temperature, time, etc. during the preparation thereof.

In a preferred embodiment, the polylactic acid derivative bound with the monovalent metal ion at its terminal carboxyl group in the invention may be represented by formula 1:

Chemical Formula 1

$$RO-CHZ-[A]_n-[B]_m-COOM$$

wherein,

A is

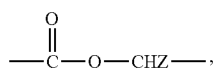

B is

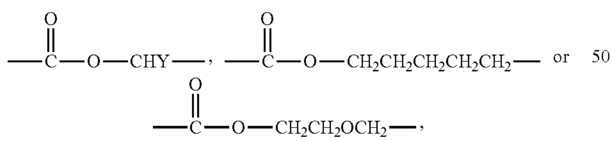

R is hydrogen, an acetyl group, benzoyl group, decanoyl group, palmitoyl group, methyl group or ethyl group, Z and Y each are hydrogens, methyl groups or phenyl groups, M is hydrogen, sodium, potassium or lithium, n is an integer of 1 to 30, and m is an integer of 1 to 20.

In another preferred embodiment, the polylactic acid derivative bound with the monovalent metal ion at its terminal carboxyl group in the invention may be represented by formula 2:

Chemical Formula 2

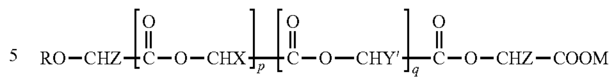

wherein,

R is hydrogen, an acetyl group, benzoyl group, decanoyl group, palmitoyl group, methyl group or ethyl group, Z is hydrogen, a methyl group or phenyl group, M is hydrogen, sodium, potassium or lithium, X is a methyl group, Y' is hydrogen or a phenyl group, p is an integer of 0 to 25, q is an integer of 0 to 25, and the sum of p and q is an integer of 5 to 25.

In another preferred embodiment, the polylactic acid derivative bound with the monovalent metal ion at its terminal carboxyl group in the invention may be represented by formula 3:

Chemical Formula

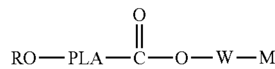

wherein,

R is hydrogen, an acetyl group, benzoyl group, decanoyl group, palmitoyl group, methyl group or ethyl group, W-M is

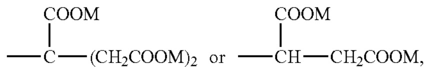

M is hydrogen, sodium, potassium or lithium, and

PLA is selected from the group consisting of D,L-polylactic acid, D-polylactic acid, polymandelic acid, a copolymer of D,L-lactic acid and glycolic acid, a copolymer of D,L-lactic acid and mandelic acid, a copolymer of D,L-lactic acid and caprolactone, and a copolymer of D,L-lactic acid and 1,4-dioxan-2-one.

In another preferred embodiment, the polylactic acid derivative bound with the monovalent metal ion at its terminal carboxyl group in the invention may be represented by formula 4:

Chemical Formula 4

$$S-O-PLA-\overset{O}{\overset{\|}{C}}-O-Q$$

S is

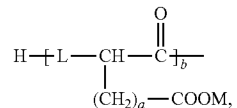

L is —$NR_1$— or —O—, $R_1$ is hydrogen or an alkyl group of $C_1$ to $C_{10}$,

Q is $CH_3$, $CH_2CH_3$, $CH_2CH_2CH_3$, $CH_2CH_2CH_2CH_3$, or $CH_2C_6H_5$,

M is hydrogen, sodium, potassium or lithium, a is an integer of 0 to 4, b is an integer of 1 to 10, and PLA is selected from the group consisting of D,L-polylactic acid, D-polylactic acid, polymandelic acid, a copolymer of D,L-lactic acid and glycolic acid, a copolymer of D,L-lactic acid and mandelic acid, a copolymer of D,L-lactic acid and caprolactone, and a copolymer of D,L-lactic acid and 1,4-dioxan-2-one.

The composition of the invention may comprise 5 to 95 wt % of the non-ionic amphiphilic block copolymer and 5 to 95 wt % of the polylactic acid derivative, with regard to the total sum 100 wt % of the non-ionic amphiphilic block copolymer and the polylactic acid derivative.

In the invention, the di- or tri-valent metal ion may be selected from the group consisting of Calcium ($Ca^{2+}$), Magnesium ($Mg^{2+}$), Barium ($Ba^{2+}$), Chrome ($Cr^{3+}$), Iron ($Fe^{3+}$), Manganese ($Mn^{2+}$), Nickel ($Ni^{2+}$), Cupper ($Cu^{2+}$), Zinc ($Zn^{2+}$) and Aluminum ($Al^{3+}$).

Such di- or tri-valent metal ion may be added in the form of sulfate, hydrochloride, carbonate, phosphate and hydroxide to the mixture polymeric composition of the amphiphilic block copolymer and the polylactic acid derivative and specifically, it may be added in the form of calcium chloride ($CaCl_2$), magnesium chloride ($MgCl_2$), zinc chloride ($ZnCl_2$), aluminum chloride ($AlCl_3$), iron chloride ($FeCl_3$), calcium carbonate ($CaCO_3$), magnesium carbonate ($MgCO_3$), calcium phosphate ($Ca_3(PO_4)_2$), magnesium phosphate ($Mg_3(PO_4)_2$), aluminum phosphate ($AlPO_4$), magnesium sulfate ($MgSO_4$), calcium hydroxide ($Ca(OH)_2$), magnesium hydroxide ($Mg(OH)_2$), aluminum hydroxide ($Al(OH)_3$) or zinc hydroxide ($Zn(OH)_2$).

Also, the di- or tri-valent metal ion may be 0.001 to 10 equivalents, preferably 0.5 to 2.0 equivalents with regard to one equivalent of the carboxyl terminal group of the polylactic derivative.

In the invention, the di- or tri-valent metal ion may be added to enhance the stability of the polymeric micelle which is formed by mixing the amphiphilic block copolymer and the polylactic acid derivative. The di- or tri-valent metal ion may bind to the terminal carboxyl group of the polylactic derivative to form a polymeric micelle bound with the di- or tri-valent metal ion. The di- or tri-valent metal ion may form an ionic bond by substitution reaction with the monovalent metal cation of the carboxyl terminal group of the polylactic acid derivative in the polymeric micelle. The formed ionic bond by the metal ion serves to enhance the stability of the polymeric micelle due to its strong binding ability.

The composition of the invention may comprise distilled water for injection, physiological saline injection, glucose injection or buffer, as the aqueous solvent.

Also, the composition of the invention may further add a pharmaceutically acceptable additive, if necessary. Preferably, at least one of a pH adjusting agent, an isotonic agent, a preservative, an analgesic, or a stabilizing agent may be further included.

The pH adjusting agent may be a pharmaceutically acceptable acid, base or buffer solution of pH 3 to 8. For example, hydrochloric acid, sodium hydroxide, acetic acid, citric acid, ascorbic acid, gluconic acid, succinic acid, tartaric acid and lactic acid, and a salt thereof may be used and preferably, a buffer solution of pH 4-7 may be used.

The isotonic agent, which is a pharmaceutically acceptable one on the assumption that the composition is to be used to a human body, may be preferably used within such a range that does not cause hematocytolysis when it is in contact with blood. Sorbitol, mannitol, xylitol, lactose, dextrose, sodium chloride, calcium chloride, potassium chloride, sodium sulfate or magnesium chloride which satisfies the above conditions may be used, but sorbitol, mannitol, dextrose or sodium chloride are preferable.

The preservative may be, for example, sodium benzoate, paraoxy methyl benzoate, etc. but is not limited thereto.

The analgesic may be, for example, benzyl alcohol, chlorobutanol, procaine hydrochloride, glucose and/or calcium gluconate, but is not limited thereto.

The stabilizing agent may be, for example, sodium bisulfite, sodium metabisulfite, sodium sulfite, nitrogen gas, and/or carbon dioxide gas, but is not limited thereto.

The bioactive agent captured in the polymeric drug carrier in the invention is preferably an insoluble drug of which the solubility in water is not higher than 50 mg/ml. For example, the bioactive agent in the invention may be selected from the group consisting of anticancer drugs, antiphlogistics, antifungal drugs, immunosuppressive drugs, anti-viral drugs, anti-inflammatory analgesic drugs, anesthetic drugs, hormones, anti-diabetic drugs, anti-hypertensive drugs, antiemetic drugs, and antibiotics.

More particularly, the bioactive agent in the invention may be anticancer drugs such as paclitaxel, docetaxel, ixabepilone, epothilone, camptothecin, etoposide, doxorubicin, daunorubicin, idarubicin, ara-C, etc.; immunosuppressive drugs such as cyclosporin A, sirolimus, temsirolimus, everolimus, etc.; anti-fungal drugs such as itraconazole, fluconazole, voriconazole, posaconazole, ketoconazole, etc.; steroid hormone drugs such as testosterone, estradiol, estrogen, progesterone, triamcinolone acetate, dexamethasone, etc.; anti-inflammatory analgesic drugs such as tenoxicam, piroxicam, indomethacin, ibuprofen and COX-II inhibitor, but is not limited thereto.

The composition of the invention may comprise 0.5 to 30 wt % of the polymeric drug carrier of, 0.01 to 10 wt % of the bioactive agent, and 60 to 99.49 wt % of water. Preferably, the bioactive agent may be included in the range of 0.1 to 10 wt % with regard to the weight of the polymeric drug carrier, the amphiphilic block copolymer may be in the concentration range of 10 to 300 mg/mL, and the polylactic acid derivative bound with the monovalent metal ion at its terminal carboxyl group may be in the concentration range of 1 to 200 mg/mL.

The polymeric drug carrier in the solution composition of the invention may form a polymeric micelle or a polymeric nanoparticle and entrap the bioactive agent inside it. The sizes of the polymeric nanoparticles may be adjusted to sizes of 1 to 400 nm, depending on the molecular weights of the polymers and preferably they may be in the range of 5 to 200 nm.

The solution composition of the invention may be administered orally or parenterally. The parenteral administration routes include intravenous, intramuscular, subcutaneous, intraperitoneal, intrarectal, transnasal, intraocular, or intrapulmonary routes.

The aqueous solution composition of the invention is characterized by maintaining its storage stability even in its aqueous solution state for at least 6 months, preferably at least 12 months when stored under refrigeration due to its improved storage stability. The refrigeration storage may be conducted at a temperature below the room temperature, preferably 0 to 10° C., more preferably 2 to 8° C.

Therefore, the invention provides a pharmaceutical solution composition for storage under refrigeration having storage stability for at least 6 months, preferably at least 12 months when stored under refrigeration, comprising a polymeric drug carrier, a bioactive agent entrapped inside the drug carrier, and an aqueous solvent, wherein the polymeric drug carrier comprises (a) a non-ionic amphiphilic block copolymer which is comprised of a hydrophilic block and a hydrophobic block, and (b) a polylactic acid derivative having a di- or tri-valent metal ion substituted for a monovalent metal ion which is bound to the polylactic acid derivative at its terminal carboxyl group.

According to a specific example, the polymeric drug carrier solution compositions of the invention hardly showed any changes in properties and particle sizes for at least 6 months, preferably at least 12 months as time passed by under refrigeration conditions in spite of being in their aqueous solution state. Particularly, the polymeric nanoparticle solution compositions entrapped with paclitaxel, docetaxel, or sirolimus as a bioactive agent did not show any drug precipitation for at least 6 months, preferably at least 12 months.

Such results showed that the polymeric nanoparticles maintained the properties and stability of the nanoparticles even in their aqueous solution state for a sufficiently long period of time and moreover, if insoluble drugs are entrapped in the polymeric nanoparticles, the drugs are not exposed to water phase until the polymers are degraded so it is possible to stabilize unstable insoluble drugs and store them in their aqueous solution state for a long time.

The pharmaceutical composition of the invention may be prepared by a preparation method comprising (1) dissolving a non-ionic amphiphilic block copolymer which is comprised of a hydrophilic block and a hydrophobic block, and a polylactic acid derivative bound with a monovalent metal ion at its terminal carboxyl group in an organic solvent;

(2) dissolving a bioactive agent in the solution of step (1);

(3) eliminating the organic solvent from the solution of step (2) and adding an injection solution to form a polymeric matrix containing the bioactive agent; and (4) adding a di- or tri-valent metal ion salt. Specifically, the method for preparing the polymeric solution composition comprises dissolving the amphiphilic block copolymer, the polylactic acid derivative and the bioactive agent in an organic solvent, completely eliminating the organic solvent, and adding an injection solution such as water to the remaining dry substance to form a polymeric matrix. Subsequently, a di- or tri-metal ion salt may be added to the polymeric matrix thereby to enhance the stability of the polymeric micelle.

The organic solvent may be selected from the group consisting of dichloromethane, alcohols, acetone, tetrahydrofuran, acetic acid, acetonitrile and dioxane, and the alcohols may include one or a mixture of two or more selected from the group consisting of methanol, ethanol, propanol and butanol, but are not limited thereto.

Further, after the step (4), a pharmaceutically acceptable additive may be suitably added, if necessary. Preferably, at least one of a pH adjusting agent, an isotonic agent, a preservative, an analgesic or a stabilizing agent may be added.

The known polymeric drug carrier containing pharmaceutical composition was prepared by dissolving a drug and a polymer in an organic solvent, eliminating the organic solvent and then adding an aqueous solution to produce a polymeric nanoparticle solution, which was then prepared into a porous cake or powder type through lyophilization process. However, it takes huge time for the lyophilization process, and also takes a considerably huge amount of the manufacturing cost because it essentially requires lyophilization machines. In comparison, the pharmaceutical composition in a solution form of the invention has a merit in that it is applicable to a human body right away without undergoing any reconstitution or dilution steps because of the lack of lyophilization process. Also, because it does not need lyophilization, it can considerably reduce its manufacturing time and cost, and it can be conveniently used because no reconstitution is needed for its use.

BEST MODE TO CARRY OUT THE INVENTION

The invention will be described in more detail by examples. The following examples are intended to merely illustrate the present invention, and the scope of the invention is not limited by them in any ways.

The amphiphilic block copolymer and the polylactic acid salt bound with an alkali metal ion at its carboxylic acid terminal or the derivative thereof used in the examples of the invention were prepared by the methods disclosed in WO03/033592. The entire content of this application is incorporated hereinto by reference.

Examples 1 to 3

Preparation of Paclitaxel Polymeric Nanoparticle Aqueous Solution Composition A monomethoxy polyethyleneglycol-polylactide having a number average molecular weight of 2,000-1,800 Daltons was synthesized as an amphiphilic block copolymer. Also, D,L-PLA-COONa having a number average molecular weight of 1,500 Daltons was synthesized. The amphiphilic block copolymer and the polylactic acid salt bound with an alkali metal ion at its carboxylic acid terminal or the derivatives thereof were prepared by the methods disclosed in WO 03/033592.

The polylactic acid derivative and the amphiphilic block copolymer were stirred in the amounts as set forth in table 1 below at 50° C. and thus completely dissolved, and then completely mixed with 10 mL of dichloromethane. Paclitaxel was added to the polymeric dichloromethane solutions, which were then stirred until the paclitaxel was completely dissolved and became clear solutions. The dichloromethane was distilled under a reduced pressure using a vacuum pump and thus completely eliminated, and then a purified water of a room temperature was added thereto to form micelles until they became clear blue solutions. A calcium chloride solution was added to the produced solutions to form paclitaxel containing polymeric nanoparticles. The polymeric nanoparticle solutions were completely dissolved by adding sodium chloride as an isotonic agent thereto. Then, the pH of the polymeric nanoparticle solutions was adjusted by adding 1N-sodium hydroxide as a pH adjusting agent thereto, and then they were filtered using a filter with a pore size of 200 nm to produce polymeric nanoparticle aqueous solution compositions containing paclitaxel.

TABLE 1

| Category | Amounts used (mg) | | | | | | |
|---|---|---|---|---|---|---|---|
| | Paclitaxel | Polylactic acid derivative[1] | Amphiphilic block copolymer[2] | Metal ion salt[3] | Isotonic agent[4] | Purified water | pH adjusting agent[5] |
| Ex. 1 | 100.0 | 4,950.0 | 4,950.0 | 366.27 | 810 | 90,000 | 20.0 |
| Ex. 2 | 100.0 | 3,300.0 | 6,600.0 | 244.18 | 810 | 90,000 | 20.0 |
| Ex. 3 | 100.0 | 2,475.0 | 7,425.0 | 183.13 | 810 | 90,000 | 20.0 |

[1]D,L-PLA-COONa, number average molecular weight 1,500 Daltons
[2]Monomethoxypolyethyleneglycol-polylactide, number average molecular weight 2,000-1,800 Daltons
[3]Calcium chloride
[4]Sodium chloride
[5]Sodium hydroxide

Examples 4 and 5

Preparation of Paclitaxel Polymeric Nanoparticle Buffer Aqueous Solution Composition A monomethoxy polyethyleneglycol-polylactide having a number average molecular weight of 2,000-1,800 Daltons was synthesized as an amphiphilic block copolymer. Also, D,L-PLA-COONa having a number average molecular weight of 1,500 Daltons was synthesized. The amphiphilic block copolymer and the polylactic acid salt bound with an alkali metal ion at its carboxylic acid terminal or the derivatives thereof were prepared by the methods disclosed in WO 03/033592.

The polylactic acid derivative and the amphiphilic block copolymer were stirred in the amounts as set forth in table 2 below at 50° C. and thus completely dissolved, and then completely mixed with 10 mL of dichloromethane. Paclitaxel was added to the polymeric dichloromethane solutions, which were then stirred until the paclitaxel was completely dissolved and became clear solutions. The dichloromethane was distilled under a reduced pressure using a vacuum pump and thus completely eliminated, and then a citric acid buffer (0.1M, pH 6.0) (Example 4) and an succinic acid buffer (0.15M, pH 6.0) (Example 5) of a room temperature were each added thereto to form micelles until they became clear blue solutions. A calcium chloride solution was added to the produced solutions to form paclitaxel containing polymeric nanoparticles. Then, the pH of the polymeric nanoparticle solutions was adjusted by adding 1N-sodium hydroxide as a pH adjusting agent thereto, and then they were filtered using a filter with a pore size of 200 nm to produce polymeric nanoparticle solution compositions containing paclitaxel.

TABLE 2

| Category | Amounts used (mg) | | | | | |
|---|---|---|---|---|---|---|
| | Paclitaxel | Polylactic acid derivative[1] | Amphiphilic block copolymer[2] | Metal ion salt[3] | Citric acid buffer[4] | Succinic acid buffer[4] |
| Ex. 4 | 100.0 | 1,900.0 | 8,000.0 | 215.0 | 89,785 | — |
| Ex. 5 | 100.0 | 1,900.0 | 8,000.0 | 215.0 | — | 89,785 |

[1]D,L-PLA-COONa, number average molecular weight 1,500 Daltons
[2]Monomethoxypolyethyleneglycol-polylactide, number average molecular weight 2,000-1,800 Daltons
[3]Calcium chloride
[4]The buffer serves as an aqueous solvent and a pH adjusting agent, and the pH was finely adjusted with another pH adjusting agent in case that the pH of the buffer changes when mixed with the polymers.

Examples 6 to 8

Preparation of Docetaxel Polymeric Nanoparticle Aqueous Solution Composition A monomethoxy polyethyleneglycol-polylactide having a number average molecular weight of 2,000-1,800 Daltons was synthesized as an amphiphilic block copolymer. Also, D,L-PLA-COONa having a number average molecular weight of 1,500 Daltons was synthesized. The amphiphilic block copolymer and the polylactic acid salt bound with an alkali metal ion at its carboxylic acid terminal or the derivatives thereof were prepared by the methods disclosed in WO 03/033592.

The polylactic acid derivative and the amphiphilic block copolymer were stirred in the amounts as set forth in table 3 below at 50° C. and thus completely dissolved, and then completely mixed with 10 mL of dichloromethane. Docetaxel was added to the polymeric dichloromethane solutions, which were then stirred until the docetaxel was completely dissolved and became clear solutions. The dichloromethane was distilled under a reduced pressure using a vacuum pump and thus completely eliminated, and then a citric acid buffer (0.1M, pH 6.0) of a room temperature was added thereto to form micelles until they became clear blue solutions. A calcium chloride solution was added to the produced solutions to form docetaxel containing polymeric nanoparticles. The polymeric nanoparticle solutions were completely dissolved by adding sodium chloride as an isotonic agent thereto. Then, the pH of the polymeric nanoparticle solutions was adjusted by adding 1N-sodium hydroxide as a pH adjusting agent thereto, and then they were filtered using a filter with a pore size of 200 nm to produce polymeric nanoparticle aqueous solution compositions containing docetaxel.

TABLE 3

| Category | Amounts used (mg) | | | | | |
|---|---|---|---|---|---|---|
| | Docetaxel | Polylactic acid derivative[1] | Amphiphilic block copolymer[2] | Metal ion salt[3] | Isotonic agent[4] | Buffer[5] |
| Ex. 6 | 100.0 | 4,950.0 | 4,950.0 | 366.27 | 810 | 90,000 |
| Ex. 7 | 100.0 | 3,300.0 | 6,600.0 | 244.18 | 810 | 90,000 |
| Ex. 8 | 100.0 | 2,475.0 | 7,425.0 | 183.13 | 810 | 90,000 |

[1]D,L-PLA-COONa, number average molecular weight 1,500 Daltons
[2]Monomethoxypolyethyleneglycol-polylactide, number average molecular weight 2,000-1,800 Daltons
[3]Calcium chloride
[4]Sodium chloride
[5]Citric acid buffer (0.1M, pH 6.0) serves as an aqueous solvent and pH adjusting agent, and the pH was finely adjusted with another pH adjusting agent in case that the pH of the buffer changes when mixed with the polymers.

Examples 9 to 11

Preparation of Sirolimus Polymeric Nanoparticle Aqueous Solution Composition

A monomethoxy polyethyleneglycol-polylactide having a number average molecular weight of 2,000-1,800 Daltons was synthesized as an amphiphilic block copolymer. Also, D,L-PLA-COONa having a number average molecular weight of 1,500 Daltons was synthesized. The amphiphilic block copolymer and the polylactic acid salt bound with an alkali metal ion at its carboxylic acid terminal or the derivatives thereof were prepared by the methods disclosed in WO 03/033592.

The polylactic acid derivative and the amphiphilic block copolymer were stirred in the amounts as set forth in table 4 below at 50° C. and thus completely dissolved, and then completely mixed with 10 mL of dichloromethane. Sirolimus was added to the polymeric dichloromethane solutions, which were then stirred until the sirolimus was completely dissolved and became clear solutions. The dichloromethane was distilled under a reduced pressure using a vacuum pump and thus completely eliminated, and then an acetic acid buffer (0.2M, pH 5.6) of a room temperature was added thereto to form micelles until they became clear blue solutions. A calcium chloride solution was added to the produced solutions to form sirolimus containing polymeric nanoparticles. The polymeric nanoparticle solutions were completely dissolved by adding glucose as an isotonic agent thereto. Then, the pH of the polymeric nanoparticle solutions was adjusted by adding 1N-sodium hydroxide as a pH adjusting agent thereto, and then they were filtered using a filter with a pore size of 200 nm to produce polymeric nanoparticle aqueous solution compositions containing sirolimus.

TABLE 4

| Category | Amounts used (mg) | | | | | |
|---|---|---|---|---|---|---|
| | Sirolimus | Polylactic acid derivative[1)] | Amphiphilic block copolymer[2)] | Metal ion salt[3)] | Isotonic agent[4)] | Buffer[5)] |
| Ex. 9 | 100.0 | 4,950.0 | 4,950.0 | 366.27 | 4,500 | 90,000 |
| Ex. 10 | 100.0 | 3,300.0 | 6,600.0 | 244.18 | 4,500 | 90,000 |
| Ex. 11 | 100.0 | 2,475.0 | 7,425.0 | 183.13 | 4,500 | 90,000 |

[1)] D,L-PLA-COONa, number average molecular weight 1,500 Daltons

[2)] Monomethoxypolyethyleneglycol-polylactide, number average molecular weight 2,000-1,800 Daltons

[3)] Calcium chloride

[4)] Glucose

[5)] Acetic acid buffer (0.2M, pH 5.6) serves as an aqueous solvent and pH adjusting agent, and the pH was finely adjusted with another pH adjusting agent in case that the pH of the buffer changes when mixed with the polymers.

Experiment Example 1

Stability Test of Aqueous Solution Composition for Paclitaxel-Containing Polymeric Nanoparticles The paclitaxel containing polymeric nanoparticle solution compositions of Examples 1 to 3 above, and an injection solution prepared by diluting a commercial product (Taxol) in a physiological saline injection so that the paclitaxel concentration became 1 mg/ml were each stored in a refrigerator (5±3° C.) and evaluated for their stability over 12 months. The results were set forth in Tables 5 to 8 below.

TABLE 5

| Time (month) | Appearance of solutions | | | |
|---|---|---|---|---|
| | Ex. 1 | Ex. 2 | Ex. 3 | Commercial product |
| 0 | Clear | Clear | Clear | Clear |
| 1 | Clear | Clear | Clear | Precipitate |
| 2 | Clear | Clear | Clear | Precipitate |
| 4 | Clear | Clear | Clear | Precipitate |
| 6 | Clear | Clear | Clear | Precipitate |
| 9 | Clear | Clear | Clear | Precipitate |
| 12 | Clear | Clear | Clear | Precipitate |

TABLE 6

| Time | pH | | | |
|---|---|---|---|---|
| (month) | Ex. 1 | Ex. 2 | Ex. 3 | Commercial product |
| 0 | 6.5 | 6.6 | 6.7 | 4.6 |
| 1 | 6.3 | 6.2 | 6.5 | — |
| 2 | 5.9 | 5.8 | 6.0 | — |
| 4 | 5.4 | 5.4 | 5.6 | — |
| 6 | 4.8 | 5.0 | 5.0 | — |
| 9 | 4.6 | 4.7 | 4.8 | — |
| 12 | 4.3 | 4.4 | 4.5 | — |

TABLE 7

| Time | Average particle size (nm) | | | |
|---|---|---|---|---|
| (month) | Ex. 1 | Ex. 2 | Ex. 3 | Commercial product |
| 0 | 23.3 | 23.0 | 22.5 | — |
| 1 | 24.6 | 24.8 | 25.3 | — |
| 2 | 24.3 | 24.7 | 26.2 | — |
| 4 | 23.7 | 23.9 | 24.5 | — |
| 6 | 25.7 | 24.6 | 26.5 | — |
| 9 | 25.4 | 24.7 | 26.6 | — |
| 12 | 26.3 | 25.7 | 26.4 | — |

TABLE 8

| Time (month) | Drug content (wt %) | | | |
|---|---|---|---|---|
| | Ex. 1 | Ex. 2 | Ex. 3 | Commercial Product |
| 0 | 100.0 | 100.0 | 100.0 | 100.0 |
| 1 | 99.7 | 100.1 | 100.3 | 21.2 |
| 2 | 99.3 | 99.7 | 99.6 | 20.5 |
| 4 | 99.5 | 99.5 | 99.7 | 19.9 |
| 6 | 99.6 | 99.3 | 99.4 | 19.0 |
| 9 | 99.5 | 99.1 | 98.4 | 18.4 |
| 12 | 99.3 | 98.8 | 98.6 | 17.6 |

As shown in the above tables, any paclitaxel was not precipitated for 12 months in the paclitaxel containing polymeric nanoparticle solution compositions of Examples 1 to 3. In comparison, paclitaxel was precipitated even in the first month in the injection solution of the commercial product, and thus it was impossible to measure its pH after the first month and also impossible to measure its particle size because it was in a solution state with no particles. From the above results, it can be seen that the polymeric nanoparticle aqueous solution compositions of the invention are compositions capable of storing paclitaxel in an aqueous solution state for a long time.

Experiment Example 2

Stability Test of Aqueous Buffered Solution Composition for Paclitaxel-Containing Polymeric Nanoparticles The paclitaxel containing polymeric nanoparticle citric acid buffer aqueous solution composition and succinic acid buffer aqueous solution composition of Examples 4 and 5 above (paclitaxel concentration: 1 mg/ml) were each stored in a refrigerator (5±3° C.) and evaluated for their stability over 12 months. The results were set forth in Tables 9 to 12 below.

TABLE 9

| Time | Appearance of solutions | |
|---|---|---|
| (month) | Ex. 4 | Ex. 5 |
| 0 | Clear | Clear |
| 1 | Clear | Clear |
| 2 | Clear | Clear |
| 4 | Clear | Clear |
| 6 | Clear | Clear |
| 9 | Clear | Clear |
| 12 | Clear | Clear |

TABLE 10

| Time | pH | |
|---|---|---|
| (month) | Ex. 4 | Ex. 5 |
| 0 | 6.4 | 5.9 |
| 1 | 6.2 | 5.7 |
| 2 | 6.1 | 5.5 |
| 4 | 5.9 | 5.3 |
| 6 | 5.7 | 5.1 |
| 9 | 5.5 | 5.0 |
| 12 | 5.2 | 4.8 |

TABLE 11

| Time | Average particle size (nm) | |
|---|---|---|
| (month) | Ex. 4 | Ex. 5 |
| 0 | 23.4 | 23.2 |
| 1 | 23.2 | 23.3 |
| 2 | 23.3 | 24.0 |
| 4 | 23.9 | 23.5 |
| 6 | 22.3 | 22.6 |
| 9 | 25.6 | 26.4 |
| 12 | 26.2 | 27.0 |

TABLE 12

| Time | Drug content (wt %) | |
|---|---|---|
| (month) | Ex. 4 | Ex. 5 |
| 0 | 100.0 | 100.0 |
| 1 | 100.3 | 100.8 |
| 2 | 100.8 | 99.7 |
| 4 | 99.9 | 100.1 |
| 6 | 99.5 | 99.9 |
| 9 | 99.5 | 98.9 |
| 12 | 99.1 | 98.8 |

As shown in the above tables, any paclitaxel was not precipitated for 12 months in the paclitaxel containing polymeric nanoparticle aqueous solution compositions of Examples 4 and 5. Since there was hardly any chemical change in particle size or content, the type of buffer solutions seemed to have no big effect on the stability of the paclitaxel containing polymeric nanoparticle aqueous solution compositions. From the above results, it can be seen that the polymeric nanoparticle aqueous solution compositions of the invention are compositions capable of storing paclitaxel in an aqueous solution state for a long time.

Experiment Example 3

Stability Test of Aqueous Buffered Solution Composition for Docetaxel-Containing Polymeric Nanoparticles The docetaxel containing polymeric nanoparticle aqueous solution compositions of Examples 6 to 8 above, and an injection solution prepared by diluting a commercial product (Taxotere) which was a mixture solution prepared by adding a dilution vial solution to a concentrate vial and diluting with a physiological saline injection so that the docetaxel concentration became 1 mg/ml were each stored in a refrigerator (5±3° C.) and evaluated for their stability over 12 months. The results were set forth in Tables 13 to 16 below.

TABLE 13

| Time | Appearance of solutions | | | |
|---|---|---|---|---|
| (month) | Ex. 6 | Ex. 7 | Ex. 8 | Commercial product |
| 0 | Clear | Clear | Clear | Clear |
| 1 | Clear | Clear | Clear | Precipitate |
| 2 | Clear | Clear | Clear | Precipitate |
| 4 | Clear | Clear | Clear | Precipitate |
| 6 | Clear | Clear | Clear | Precipitate |
| 8 | Clear | Clear | Clear | Precipitate |
| 12 | Clear | Clear | Clear | Precipitate |

TABLE 14

| Time | pH | | | |
|---|---|---|---|---|
| (month) | Ex. 6 | Ex. 7 | Ex. 8 | Commercial Product |
| 0 | 5.6 | 5.7 | 5.8 | 4.5 |
| 1 | 5.5 | 5.5 | 5.5 | — |
| 2 | 5.1 | 5.3 | 5.2 | — |
| 4 | 4.9 | 5.0 | 4.8 | — |
| 6 | 4.6 | 4.7 | 4.5 | — |
| 8 | 4.2 | 4.3 | 4.1 | — |
| 12 | 4.0 | 4.1 | 4.0 | — |

TABLE 15

| Time | Average particle size (nm) | | | |
|---|---|---|---|---|
| (month) | Ex. 6 | Ex. 7 | Ex. 8 | Commercial Product |
| 0 | 25.6 | 23.3 | 24.2 | — |
| 1 | 25.5 | 24.5 | 24.0 | — |
| 2 | 24.8 | 26.4 | 24.3 | — |
| 4 | 23.9 | 25.2 | 24.8 | — |
| 6 | 27.7 | 26.7 | 25.3 | — |
| 8 | 27.3 | 28.1 | 26.2 | — |
| 12 | 27.5 | 27.6 | 25.8 | — |

TABLE 16

| Time (month) | Drug Content (wt %) Ex. 6 | Ex. 7 | Ex. 8 | Commercial product |
|---|---|---|---|---|
| 0 | 100.0 | 100.0 | 100.0 | 100.0 |
| 1 | 99.5 | 101.3 | 100.5 | 15.7 |
| 2 | 99.3 | 100.2 | 99.7 | 11.5 |
| 4 | 99.9 | 99.7 | 99.2 | 4.3 |
| 6 | 98.6 | 98.5 | 98.7 | 2.1 |
| 8 | 99.0 | 98.0 | 98.3 | 1.5 |
| 12 | 98.1 | 97.7 | 97.9 | 1.1 |

As shown in the above tables, any paclitaxel was not precipitated for 12 months in the docetaxel containing polymeric nanoparticle aqueous solution compositions of Examples 6 and 8. In comparison, docetaxel was precipitated even in the first month in the injection solution of the commercial product, and thus it was impossible to measure its pH after the first month and also impossible to measure its particle size because it was in a solution state with no particles. From the above results, it can be seen that the polymeric nanoparticle aqueous solution compositions of the invention are compositions capable of storing docetaxel in an aqueous solution state for a long time.

Experiment Example 4

Stability Test of Aqueous Buffered Solution Composition for Sirolimus-Containing Polymeric Nanoparticles The sirolimus containing polymeric nanoparticle aqueous solution compositions of Examples 9 to 11 above were each stored under refrigeration (5±3° C.) and evaluated for their stability over 6 months. The results were set forth in Tables 17 to 20 below.

TABLE 17

| Time (month) | Appearance of solutions Ex. 9 | Ex. 10 | Ex. 11 |
|---|---|---|---|
| 0 | Clear | Clear | Clear |
| 1 | Clear | Clear | Clear |
| 2 | Clear | Clear | Clear |
| 4 | Clear | Clear | Clear |
| 6 | Clear | Clear | Clear |

TABLE 18

| Time (month) | pH Ex. 9 | Ex. 10 | Ex. 11 |
|---|---|---|---|
| 0 | 5.5 | 5.6 | 5.6 |
| 1 | 5.5 | 5.4 | 5.5 |
| 2 | 5.4 | 5.4 | 5.3 |
| 4 | 5.2 | 5.1 | 5.2 |
| 6 | 5.0 | 5.0 | 4.9 |

TABLE 19

| Time (month) | Particle size Ex. 9 | Ex. 10 | Ex. 11 |
|---|---|---|---|
| 0 | 23.5 | 22.0 | 23.5 |
| 1 | 25.6 | 23.9 | 24.6 |
| 2 | 24.0 | 23.6 | 24.2 |
| 4 | 24.8 | 24.9 | 23.2 |
| 6 | 26.6 | 24.6 | 24.3 |

TABLE 20

| Time (month) | Drug content (wt %)* Ex. 9 | Ex. 10 | Ex. 11 |
|---|---|---|---|
| 0 | 100.0 | 100.0 | 100.0 |
| 1 | 100.5 | 100.3 | 99.8 |
| 2 | 100.4 | 100.1 | 100.4 |
| 4 | 99.9 | 99.7 | 100.5 |
| 6 | 98.5 | 98.9 | 99.6 |

*Sum of sirolimus and its isomers

As shown in the above tables, any sirolimus was not precipitated for 6 months in the sirolimus containing polymeric nanoparticle aqueous solution compositions of Examples 9 and 12. From the above results, it can be seen that the polymeric nanoparticle solution compositions of the invention are compositions capable of storing sirolimus in an aqueous solution state for a long time.

What is claimed is:

1. A method for storing a pharmaceutical composition in a stable condition for 6 months or more in an aqueous solution form for use as final product, comprising:

storing the pharmaceutical composition comprising a polymeric drug carrier, a bioactive agent entrapped inside the drug carrier, an aqueous solvent, a pH adjusting agent, and an isotonic agent under refrigeration at 0 to 10° C., wherein the polymeric drug carrier comprises (a) an non-ionic amphiphilic block copolymer containing a hydrophilic block and a hydrophobic block, and (b) a polylactic acid derivative including a di- or tri-valent metal ion substituted for a monovalent metal ion which is bound to the terminal carboxyl group of a D,L-polylactic acid, wherein the polymeric drug carrier is prepared without lyophilization, wherein the hydrophilic block is selected from the group consisting of monomethoxypolyethylene glycol and polyethylene glycol, and the hydrophobic block is polylactide; and wherein the bioactive agent is selected from the group consisting of paclitaxel, docetaxel, sirolimus, temsirolimus, and everolimus.

2. The method as claimed in claim 1, wherein the composition comprises 5 to 95 wt % of the non-ionic amphiphilic block copolymer and 5 to 95 wt % of the polylactic acid derivative, with regard to total 100 wt % of the non-ionic amphiphilic block copolymer and the polylactic acid derivative.

3. The method as claimed in claim 1, wherein the hydrophilic block and the hydrophobic block have a weight average molecular weight of 500 to 50,000 Daltons, respectively.

4. The method as claimed in claim 1, wherein the weight ratio of the hydrophilic block and the hydrophobic block included the non-ionic amphiphilic block copolymer is 2:8 to 8:2.

5. The method as claimed in claim 1, wherein the di- or tri-valent metal ion is selected from the group consisting of Calcium ($Ca^{2+}$), Magnesium ($Mg^{2+}$), Barium ($Ba^{2+}$), Chrome ($Cr^{3+}$), Iron ($Fe^{3+}$), Manganese ($Mn^{2+}$), Nickel ($Ni^{2+}$), Cupper ($Cu^{2+}$), Zinc ($Zn^{2+}$) and Aluminum ($Al^{3+}$).

6. The method as claimed in claim 1, wherein the di- or tri-valent metal ion is 0.001 to 10 equivalents with regard to 1 equivalent of the terminal carboxyl group of the polylactic acid derivative.

7. The method as claimed in claim 1, wherein the polymeric drug carrier is a polymeric micelle or a polymeric nanoparticle.

8. The method as claimed in claim 1, wherein the composition further comprises at least one of a preservative, an analgesic, and a stabilizing agent.

9. The method as claimed in claim 1, wherein the composition comprises 0.5 to 30 wt % of the polymeric drug carrier of, 0.01 to 10 wt % of the bioactive agent, and 60 to 99.49 wt % of the aqueous solvent.

10. The method as claimed in claim 1, wherein the aqueous solvent is a purified water, a distilled water for injection, physiological saline injection, glucose injection or buffer.

* * * * *